United States Patent
Ochi

(10) Patent No.: US 10,022,236 B2
(45) Date of Patent: Jul. 17, 2018

(54) INTERNAL JOINT CAVITY EXPANDER

(71) Applicants: JAPAN TISSUE ENGINEERING CO., LTD., Gamagori-shi, Aichi (JP); Mitsuo Ochi, Hiroshima-shi, Hiroshima (JP)

(72) Inventor: Mitsuo Ochi, Hiroshima (JP)

(73) Assignees: Mitsuo Ochi, Hiroshima-shi (JP); JAPAN TISSUE ENGINEERING CO., LTD., Gamagori-shi (JP)

( * ) Notice: Subject to any disclaimer, the term of this patent is extended or adjusted under 35 U.S.C. 154(b) by 18 days.

(21) Appl. No.: 15/121,229

(22) PCT Filed: Feb. 10, 2015

(86) PCT No.: PCT/JP2015/053583
§ 371 (c)(1),
(2) Date: Aug. 24, 2016

(87) PCT Pub. No.: WO2015/133231
PCT Pub. Date: Sep. 11, 2015

(65) Prior Publication Data
US 2017/0007413 A1    Jan. 12, 2017

(30) Foreign Application Priority Data
Mar. 6, 2014 (JP) .................. 2014-043655

(51) Int. Cl.
*A61F 2/38* (2006.01)
*A61B 17/64* (2006.01)

(52) U.S. Cl.
CPC ........ *A61F 2/3836* (2013.01); *A61B 17/6425* (2013.01); *A61F 2/389* (2013.01);
(Continued)

(58) Field of Classification Search
CPC .......... A61F 2/38; A61F 2/3859; A61F 2/389; A61F 2002/2892; A61F 2002/30001;
(Continued)

(56) References Cited

U.S. PATENT DOCUMENTS

| 4,024,588 A * | 5/1977 | Janssen | A61F 2/30 623/18.12 |
| 2003/0187510 A1* | 10/2003 | Hyde | A61B 17/68 623/18.12 |

(Continued)

FOREIGN PATENT DOCUMENTS

| JP | 2010-525893 A | 7/2010 |
| JP | 2011-525136 A | 9/2011 |

(Continued)

OTHER PUBLICATIONS

May 19, 2015 International Search Report issued in International Patent Application No. PCT/JP2015/053583.

(Continued)

*Primary Examiner* — Ann Schillinger
(74) *Attorney, Agent, or Firm* — Oliff PLC

(57) ABSTRACT

An internal joint cavity expander includes femur-side magnets, tibia-side magnets, and magnetic shield-members. Each femur-side magnet has a plate curved into an arc and fixed to a femur. Each tibia-side magnet has length smaller than the femur-side magnet length and having a plate curved into arc concentric with the femur-side magnet arc. Each tibia-side magnet is fixed to a tibia. The pole on the convex surface of each femur-side magnet is same as the pole on the concave surface corresponding tibia-side magnet. The convex surface of each femur-side magnet faces the concave surface of corresponding tibia-side magnet. Each magnetic shield-member covers the surface of corresponding femur-side magnet and tibia-side magnet facing the skin throughout range in which the femur-side magnet moves relative to (Continued)

the tibia-side magnet. Each magnetic shield-member prevents magnetism of corresponding magnets and from leaking outside without hindering the femur-side magnet movement relative to the tibia-side magnet.

5 Claims, 8 Drawing Sheets

(52) U.S. Cl.
CPC ........ *A61F 2/3859* (2013.01); *A61B 17/6441* (2013.01); *A61F 2210/009* (2013.01)

(58) Field of Classification Search
CPC ...... A61F 2002/3863; A61F 2002/4205; A61F 2/30; A61F 2/30749
See application file for complete search history.

(56) References Cited

U.S. PATENT DOCUMENTS

| 2008/0275567 | A1 | 11/2008 | Makower et al. |
| 2009/0318976 | A1 | 12/2009 | Gabriel et al. |
| 2010/0145464 | A1 | 6/2010 | Sidhom |

FOREIGN PATENT DOCUMENTS

| JP | 2012-157377 A | 8/2012 |
| WO | 2008/057565 A2 | 5/2008 |
| WO | 2013/187413 A1 | 12/2013 |

OTHER PUBLICATIONS

Sep. 13, 2017 Extended European Search Report issued in European Patent Application No. 15758882.3.

* cited by examiner

INTERNAL JOINT CAVITY EXPANDER

TECHNICAL FIELD

The present invention relates to an internal joint cavity expander.

BACKGROUND ART

Examples that have been provided to date as treatment for articular cartilage defects include medical treatment (such as internal medicine or joint injection) and surgical treatment (such as microfracture, mosaicplasty, or cultured cartilage transplantation). Surgical treatment requires a patient to undergo rehabilitation for restoration to usual life. It is known that, during rehabilitation, an external brace is attached to the joint to reduce the load on a treated cartilage portion. For example, PTL 1 discloses an external brace that includes a first pin, attached to a first bone portion, a second pin, attached to a second bone portion, a first magnet portion, including a first permanent magnet and attached to the first pin, and a second magnet portion, including a second permanent magnet and attached to the second pin. The first magnet portion includes a protrusion having an arcuately protruding shape in a section taken in the direction perpendicular to the longitudinal direction of the first pin. The second magnet portion includes a recess having an arcuately recessed shape in a section taken in the direction perpendicular to the longitudinal direction of the second pin. The first magnet portion and the second magnet portion are disposed so that the protrusion and the recess face each other and the same poles of the first permanent magnet and the second permanent magnet face each other. Specifically, a cylindrical magnet is prepared as the first magnet portion and a magnet having a shape obtained by cutting an arcuate portion out of a surface of a rectangular parallelepiped is prepared as the second magnet portion. The cylindrical first magnet portion is disposed so as to face the arcuate surface of the second magnet portion. Such an external brace allows the first bone portion and the second bone portion to be spaced apart from each other using repulsive force between the magnets, so that the joint is allowed to move smoothly while the load on the treated cartilage portion is being lightened (in the state where the joint cavity is expanded).

CITATION LIST

Patent Literature

PTL 1: JP 2012-157377 A

SUMMARY OF INVENTION

Technical Problem

The above-described brace, however, requires providing of hygienic care since the pins attached to the bones extend through the skin and protrude beyond the body. Moreover, braces often have a large structure, which sometimes hinders patients' daily life. In view of such circumstances, development of a brace implanted in the body (internal joint cavity expander) has been awaited. In order to apply the above-described technology of the brace to an internal joint cavity expander, the expander has to have a compact structure and to suppress a magnetic effect on the outside.

The present invention is made to solve such a problem and primarily aims to provide an internal joint cavity expander that retains the space in a knee joint between a femur and a tibia using repulsive force between magnets, the expander having a compact structure and suppressing a magnetic effect on the outside.

Solution to Problem

An internal joint cavity expander according to the present invention is an internal joint cavity expander disposed in an incision in a knee joint to retain a space in the knee joint between a femur and a tibia. The internal joint cavity expander includes a femur-side magnet, a tibia-side magnet, and a magnetic shield member. The femur-side magnet is fixed to the femur and has a shape of a plate curved into an arc so as to protrude toward the tibia. The tibia-side magnet is fixed to the tibia, is shorter in length than the femur-side magnet, and has a shape of a flat plate or a plate curved into an arc concentric with the arc of the femur-side magnet. The magnetic shield member is fixed to either the femur or the tibia. The magnetic shield member is disposed so as to cover the entirety of a surface of the femur-side magnet facing a skin and the entirety of a surface of the tibia-side magnet facing the skin throughout a range in which the femur-side magnet moves relative to the tibia-side magnet. The magnetic shield member prevents the magnetism of both magnets from leaking outside without hindering movement of the femur-side magnet relative to the tibia-side magnet. The femur-side magnet and the tibia-side magnet are disposed so as to constantly face each other and repel each other and so that the repulsive force acts in the vertical direction while the tibia-side magnet and the femur-side magnet are moving relative to each other in response to bending and stretching movements of the knee joint.

This internal joint cavity expander retains the space in the knee joint between the femur and the tibia inside an incision using the repulsive force between the magnets. Since both of the femur-side magnet and the tibia-side magnet have a plate shape, both magnets can be rendered thinner than in the case where the magnets have a cylindrical shape or a shape obtained by cutting an arcuate portion out of a surface of a rectangular parallelepiped. Thus, the internal joint cavity expander can have a compact structure. In addition, since the magnetic shield member covers the entirety of a surface of the femur-side magnet and the tibia-side magnet facing the skin, the magnetism of both magnets can be prevented from leaking outside. Furthermore, the repulsive force between the femur-side magnet and the tibia-side magnet acts in the vertical direction, that is, in a direction in which the weight is supported. Thus, even though the weight acts on the knee joint, the space in the knee joint can be securely retained.

In the internal joint cavity expander according to the present invention, the tibia-side magnet may be a magnet having a plate shape curved into an arc concentric with the arc of the femur-side magnet. This configuration allows the femur-side magnet and the tibia-side magnet to move smoothly without considerably changing the repulsive force between the magnets after the movement since the arcs of both magnets are concentric with each other.

In the internal joint cavity expander according to the present invention, the magnetic shield member may control the femur-side magnet and the tibia-side magnet so that the distance between the femur-side magnet and the tibia-side magnet does not exceed a predetermined distance. This configuration can prevent the relative position of the femur-side magnet and the tibia-side magnet from changing considerably. Thus, the space between the femur and the tibia can be retained using the repulsive force between the magnets even after repeated movements of the knee joint.

In the internal joint cavity expander according to the present invention, the femur-side magnet may be integrated with a femur-side attachment piece having a shape of a flat plate and fixed to the femur and the tibia-side magnet may be integrated with a tibia-side attachment piece having a shape of a flat plate and fixed to the tibia. Since the attachment pieces can be rendered thin, the internal joint cavity expander can have a more compact structure.

DESCRIPTION OF EMBODIMENTS

Figure 1:
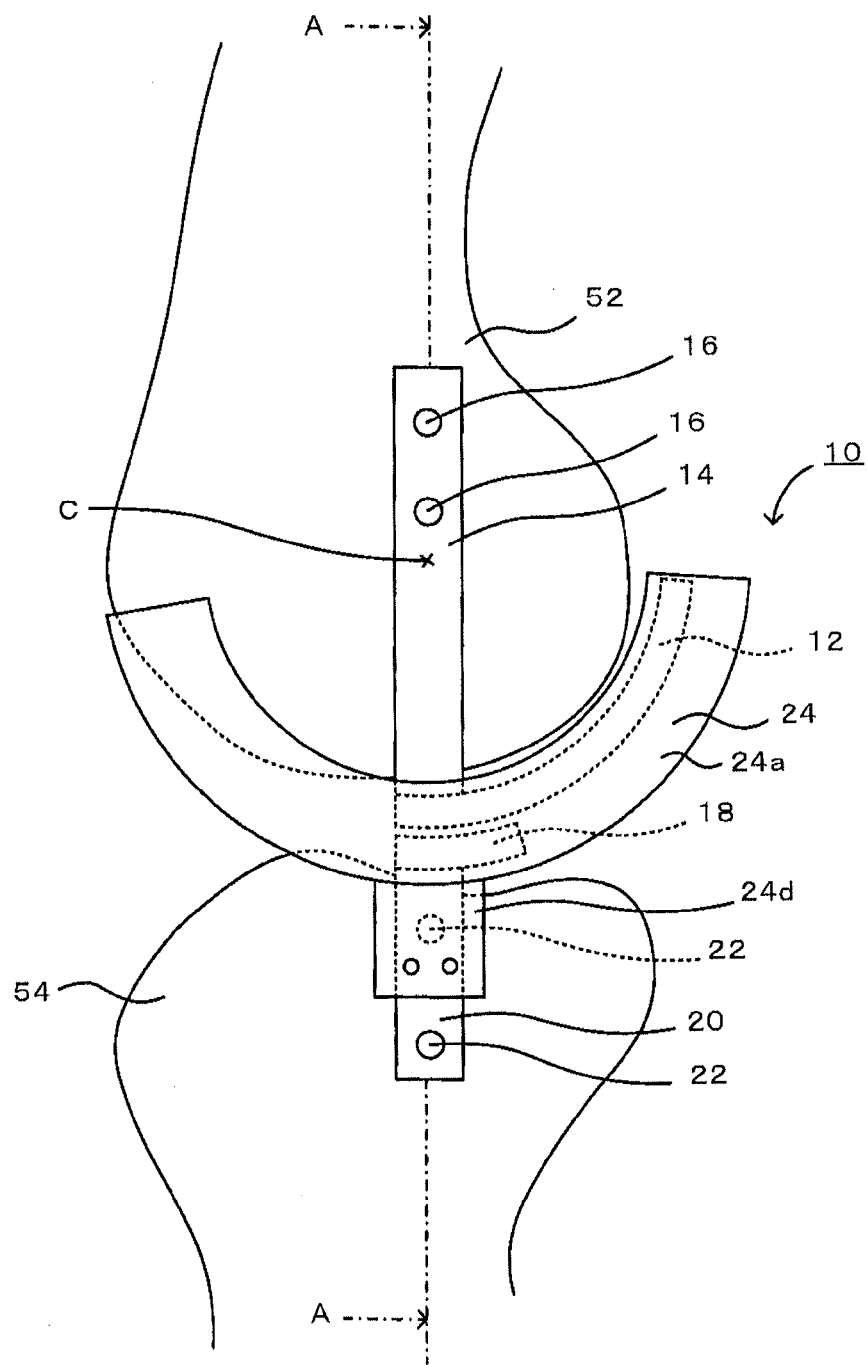
FIG. 1 is a left side view of an internal joint cavity expander 10 attached to a knee joint in a straight state.
Figure 2:
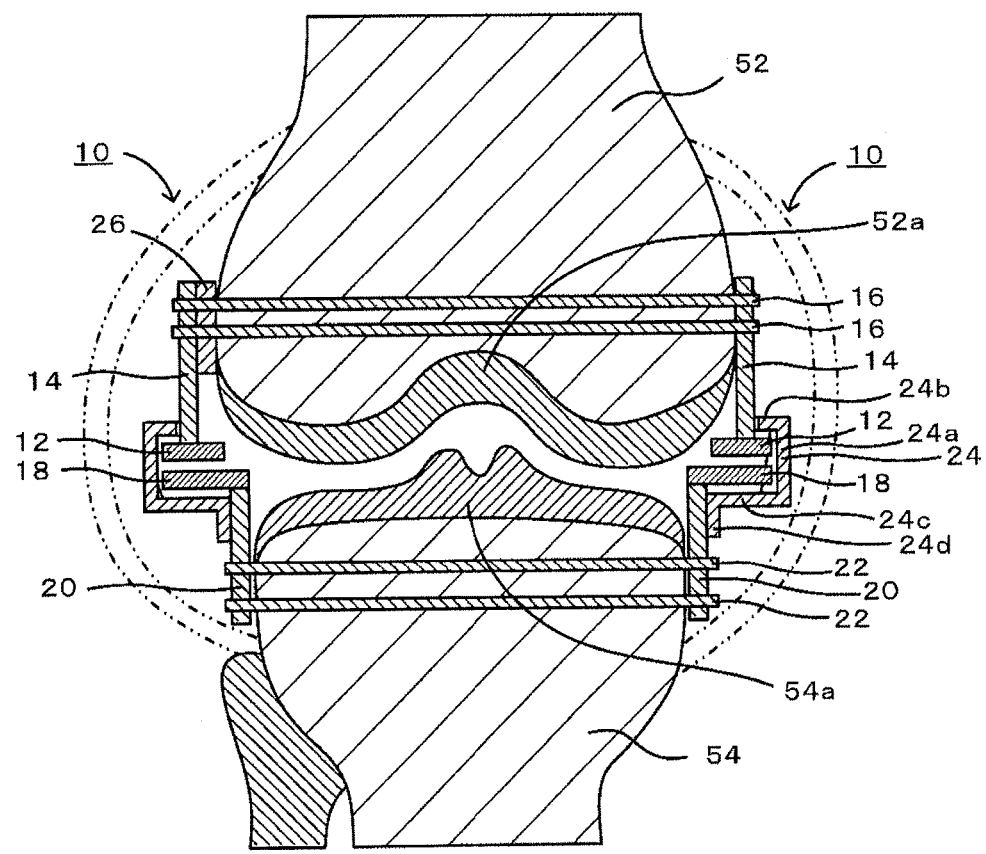
FIG. 2 is a sectional view of the internal joint cavity expander 10 taken along line A-A in FIG. 1.
Figure 3:
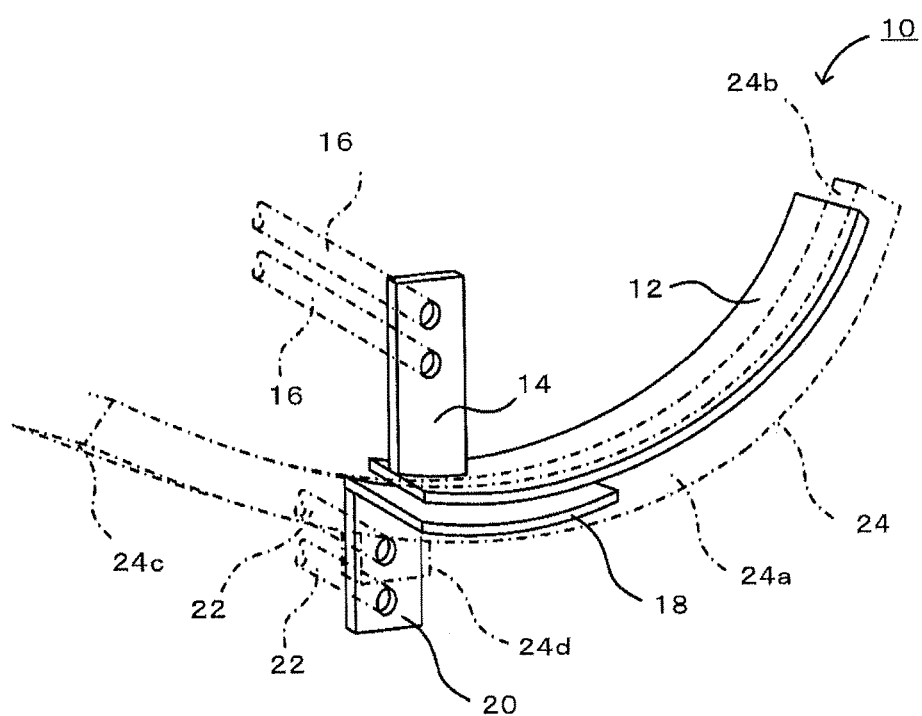
FIG. 3 is a perspective view of the internal joint cavity expander 10.

Referring to the drawings, a preferable embodiment of the present invention is described below. FIG. 1 is a left side view of an internal joint cavity expander 10 attached to a knee joint, FIG. 2 is a sectional view of the internal joint cavity expander 10 taken along line A-A in FIG. 1, and FIG. 3 is a perspective view of the internal joint cavity expander 10.

The internal joint cavity expander 10 is disposed on the left side and the right side of a knee joint consisted of a femur 52 and a tibia 54. The internal joint cavity expander 10 includes femur-side magnets 12, tibia-side magnets 18, and magnetic shield members 24. As illustrated in FIG. 2, the internal joint cavity expander 10 is completely encapsulated in a joint capsule (see a two-dot chain line).

Each femur-side magnet 12 is a permanent magnet having a plate shape curved into an arc so as to protrude toward the tibia. Each femur-side magnet 12 has a south pole on a convex surface (lower surface) and a north pole on a concave surface (upper surface). The convex surface and the concave surface of the femur-side magnet 12 have a larger area than the left and right side surfaces. Each femur-side magnet 12 also includes a femur-side attachment piece 14 of a thin plate shape. The femur-side attachment pieces 14 disposed on the left and right sides of the femur 52 are fixed to the femur 52 with two wire pins 16 that extend through the femur 52 in the horizontal direction, The two pins 16 extend through the femur 52 in such a position that a cartilage 52a of the femur 52 is not pierced. In this manner, each femur-side magnet 12 is fixed to the femur 52 using the corresponding femur-side attachment piece 14.

Each tibia-side magnet 18 is a permanent magnet shorter in length than the corresponding femur-side magnet 12 and having a plate shape curved into an arc concentric with the arc of the femur-side magnet 12. Each tibia-side magnet 18 has a north pole on a convex surface (lower surface) and a south pole on a concave surface (upper surface). The convex surface and the concave surface of the tibia-side magnet 18 have a larger area than the left and right side surfaces. Each tibia-side magnet 18 includes a tibia-side attachment piece 20 of a thin plate shape. The tibia-side attachment pieces 20 disposed on the left and right sides of the tibia 54 are fixed to the tibia 54 with two wire pins 22 that extend through the tibia 54 in the horizontal direction. The two pins 22 extend through the tibia 54 in such a position that a cartilage 54a of the tibia 54 is not pierced. In this manner, each tibia-side magnet 18 is fixed to the tibia 54 using the corresponding tibia-side attachment piece 20.

Each femur-side magnet 12 and the corresponding tibia-side magnet 18 are disposed so as to constantly face each other and repel each other while the femur-side magnet 12 and the tibia-side magnet 18 move relative to each other in response to bending and stretching movements of the knee joint. Since the same pole is disposed on the convex surface of the femur-side magnet 12 and the concave surface of the tibia-side magnet 18, the repulsive force between the magnets acts, so that both magnets keep being spaced apart from each other. Desirably, the width of the concave surface of the tibia-side magnet 18 is larger than the width of the concave surface of the femur-side magnet 12.

Those producing repulsive force of such a degree that the distance between both magnets 12 and 18 is retained even when a knee joint bears a load calculated from the weight of a patient or the like may be suitably selected as the femur-side magnet 12 and the tibia-side magnet 18. The repulsive force between both magnets 12 and 18 increases with decreasing space. Thus, the repulsive force can be calculated from an intended minimum space and an estimated load.

As illustrated in FIG. 2, the positional relationship between each femur-side magnet 12 and the corresponding tibia-side magnet 18 is determined such that the convex surface of the femur-side magnet 12 is placed within the range immediately above the concave surface of the tibia-side magnet 18. The femur-side magnet 12 on the right in FIG. 2 satisfies this positional relationship even without there being a spacer between the femur-side attachment piece 14 and the femur 52. The femur-side magnet 12 on the left, on the other hand, satisfies this positional relationship with there being a spacer 26 between the femur-side attachment piece 14 and the femur 52. Although one spacer 26 is used here, the number of spacers or the thickness of each spacer 26 may be appropriately determined in accordance with the shape of the joint. One or more spacers may also be disposed between each tibia-side attachment piece 20 and the tibia 54 as needed.

Each magnetic shield member 24 is disposed so as to cover the entirety of a surface of the femur-side magnet 12 facing the skin and the entirety of a surface of the tibia-side magnet 18 facing the skin throughout the range in which the femur-side magnet 12 moves relative to the tibia-side magnet 18. Such a range is determined in accordance with a movable range in which the femur 52 moves relative to the tibia 54. Each magnetic shield member 24 includes a face member 24a, disposed so that its upper side and its lower side are concentric with the arcs of both magnets 12 and 18, an upper bent portion 24b, bent at the upper side of the face member 24a toward the femur 52, a lower bent portion 24c, bent at the lower side of the face member 24a toward the tibia 54, and an attachment portion 24d, extending downward from the lower bent portion 24c. The attachment portion 24d of each magnetic shield member 24 is fixed to the tibia-side attachment piece 20 with a screw. Thus, each magnetic shield member 24 is integrated with the tibia 54 and is separate from the femur 52. Each magnetic shield member 24 having this configuration is made of a material that blocks magnetism and that has little effect on the human body. Examples usable as such a material include a ferromagnetic material, a paramagnetic material, and a diamagnetic material, although the material is not particularly limited to these. Examples of a ferromagnetic material include alloys containing iron, cobalt, and/or nickel. When such a material is used, desirably, inner surfaces of each magnetic shield member 24 facing magnets are plated or coated with resin or another material to prevent the magnets from adhering to the surfaces. Examples of a paramagnetic material include titanium, aluminum, platinum, and stainless steel. Examples of a diamagnetic material include gold, silver, copper, and carbon fiber.

Figure 4:
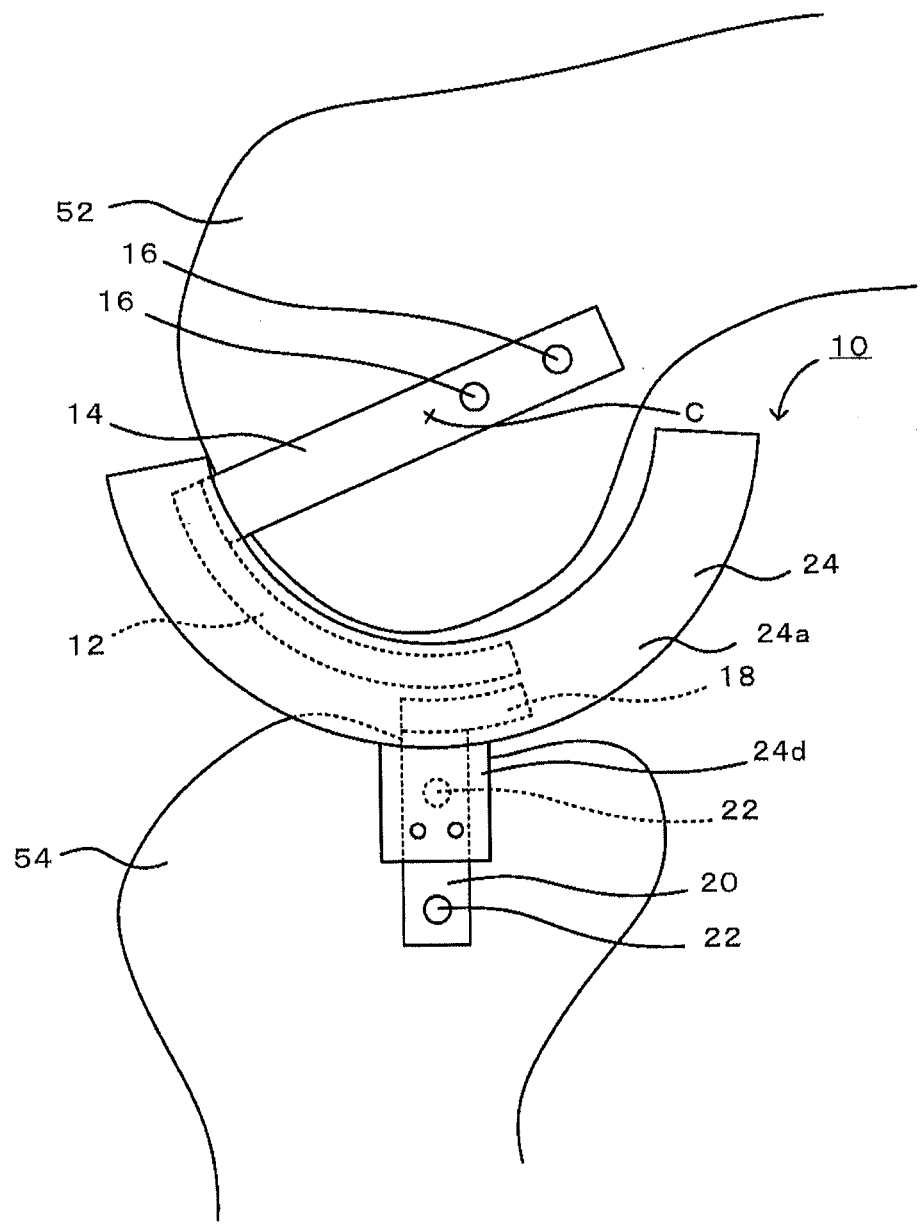
FIG. 4 is a left side view of the internal joint cavity expander 10 attached to a knee joint in a bent state.

Subsequently, an example in which the internal joint cavity expander 10 is used after cultured cartilage transplant surgery is described. FIG. 1 is a left side view of a knee joint in a straight state and FIG. 4 is a left side view of a knee joint in a bent state. In this embodiment, the internal joint cavity expander 10 is implanted in an incision in a knee joint. In the case where at least one of the cartilage 52*a* of the femur 52 or the cartilage 54*a* of the tibia 54 is damaged, cultured cartilage is transplanted into the damaged portion and the internal joint cavity expander 10 is attached so that the femur 52 and the tibia 54 do not touch each other until the cultured cartilage is fixed to the damaged portion. During an attachment of the internal joint cavity expander 10, the internal joint cavity expander 10 is fixed such that the centers of the arcs of the femur-side magnet 12 and the tibia-side magnet 18 are positioned at substantially the center (point C) of the movable circle of the tibia 54 and the femur 52. The internal joint cavity expander 10 is used to retain the space between the femur 52 and the tibia 54 and is removed when the portion to which the cultured cartilage is transplanted is cured.

When the knee joint to which the internal joint cavity expander 10 is attached is gradually bent from the straight state, the femur 52 rotates clockwise in FIG. 1 around the point C and arrives at the bendable limit as illustrated in FIG. 4. For illustrative convenience, the tibia 54 is assumed to be stationary while the knee joint is being bent. During this period, the position of each tibia-side magnet 18 is not changed and the position of the corresponding magnetic shield member 24 integrated with the tibia-side magnet 18 is not changed, either. on the other hand, each femur-side magnet 12 rotates in accordance with the rotation of the femur 52 since the femur-side magnet 12 is fixed to the femur 52. The convex surface of each femur-side magnet 12, the concave surface of the corresponding tibia-side magnet 18, and the upper and lower sides of the face member 24*a* of the corresponding magnetic shield member 24 are attached so as to foam arcs having their centers at the point C (see FIG. 1 and FIG. 4). Thus, when the femur 52 rotates around the point C, the convex surface of each femur-side magnet 12 moves while being spaced apart from the concave surface of the corresponding tibia-side magnet 18 with the effect of the repulsive force between the magnets without being interfered with the concave surface of the tibia-side magnet 18 or the corresponding magnetic shield member 24. While each femur-side magnet 12 moves relative to the corresponding tibia-side magnet 18, the convex surface of the femur-side magnet 12 and the concave surface of the tibia-side magnet 18 constantly face each other. At this time, the area over which the convex surface of the femur-side magnet 12 and the concave surface of the tibia-side magnet 18 face each other remains substantially constant during bending and stretching movements of the knee joint. Thus, the repulsive force between the magnets remains substantially constant during the bending and stretching movements of the knee joint. The direction of the repulsive force is a substantially vertical direction. The weight of the patient acts vertically downward, that is, in the direction in which the femur 52 and the tibia 54 approach each other. However, the repulsive force that cancels out this effect acts between the magnets 12 and 18 of the internal joint cavity expander 10. Thus, the femur 52 and the tibia 54 are continuously kept being spaced apart from each other. The upper and lower bent portions 24*b* and 24*c* of the magnetic shield member 24 are controlled so that the distance between the femur-side magnet 12 and the tibia-side magnet 18 does not exceed a predetermined distance. Here, the predetermined distance is calculated by subtracting the thickness of the femur-side magnet 12 and the thickness of the tibia-side magnet 18 from the distance between the upper bent portion 24*b* and the lower bent portion 24*b*.

The internal joint cavity expander 10 according to this embodiment described in detail thus far retains the space in the knee joint between the femur 52 and the tibia 54 in an incision using the repulsive force between the magnets 12 and 18. Here, both magnets 12 and 18 have a plate shape. Thus, the magnets 12 and 18 can be rendered thinner than in the case where the magnets 12 and 18 have a cylindrical shape or a shape obtained by cutting an arcuate portion out of a surface of a rectangular parallelepiped. The internal joint cavity expander 10 can thus have a compact structure. In addition, since each magnetic shield member 24 covers the entirety of a surface of the corresponding magnets 12 and 18 facing the skin, the magnetism of the magnets 12 and 18 is prevented from leaking outside.

The upper and lower bent portions 24*b* and 24*c* of each magnetic shield member 24 control the distance between the corresponding femur-side magnet 12 and the corresponding tibia-side magnet 18 so that the distance does not exceed a predetermined distance. This configuration thus prevents the relative position of each femur-side magnet 12 and the corresponding tibia-side magnet 18 from changing considerably. Thus, the space between the femur 52 and the tibia 54 can be retained using the repulsive force between the magnets even after repeated movements of the knee joint.

Each femur-side magnet 12 is integrated with the corresponding femur-side attachment piece 14 having a shape of a flat plate and fixed to the femur 52 and each tibia-side magnet 18 is integrated with the corresponding tibia-side attachment piece 20 having a shape of a flat plate and fixed to the tibia 54. Thus, the attachment pieces 14 and 20 can be rendered thin, so that the internal joint cavity expander 10 can have a more compact structure.

In addition, each magnetic shield member 24 is fixed to the tibia 54, not to the femur 52. Thus, when the femur 52 moves relative to the tibia 54, each magnetic shield member 24 does not move, so that the load otherwise imposed on tissue around the joint can be suppressed.

In addition, the repulsive force acts between the magnets 12 and 18 in a substantially vertical direction. The vertical direction is the direction in which the weight acts so that the space in the joint is likely to be reduced. Thus, the application of the present invention is highly significant.

Furthermore, the width of the concave surface of the tibia-side magnet 18 is larger than the width of the convex surface of the femur-side magnet 12. Thus, the femur-side magnet 12 and the tibia-side magnet 18 are kept facing each other and the repulsive force between the magnets does not vanish even when the convex surface of the femur-side magnet 12 is displaced in the widthwise direction to some extent as a result of the femur-side magnet 12 moving relative to the tibia-side magnet 18.

Moreover, since the internal joint cavity expander 10 is implanted in the body (in an incision), the joint portion (transplanted portion) is allowed to be immersed in, for example, a water tank or bath. The internal joint cavity expander 10 is thus hygienically advantageous compared to an external brace.

The present invention is not limited to the above-described embodiment and naturally allowed to be embodied in various modes that belong to the technical scope of the present invention.

Figure 5:
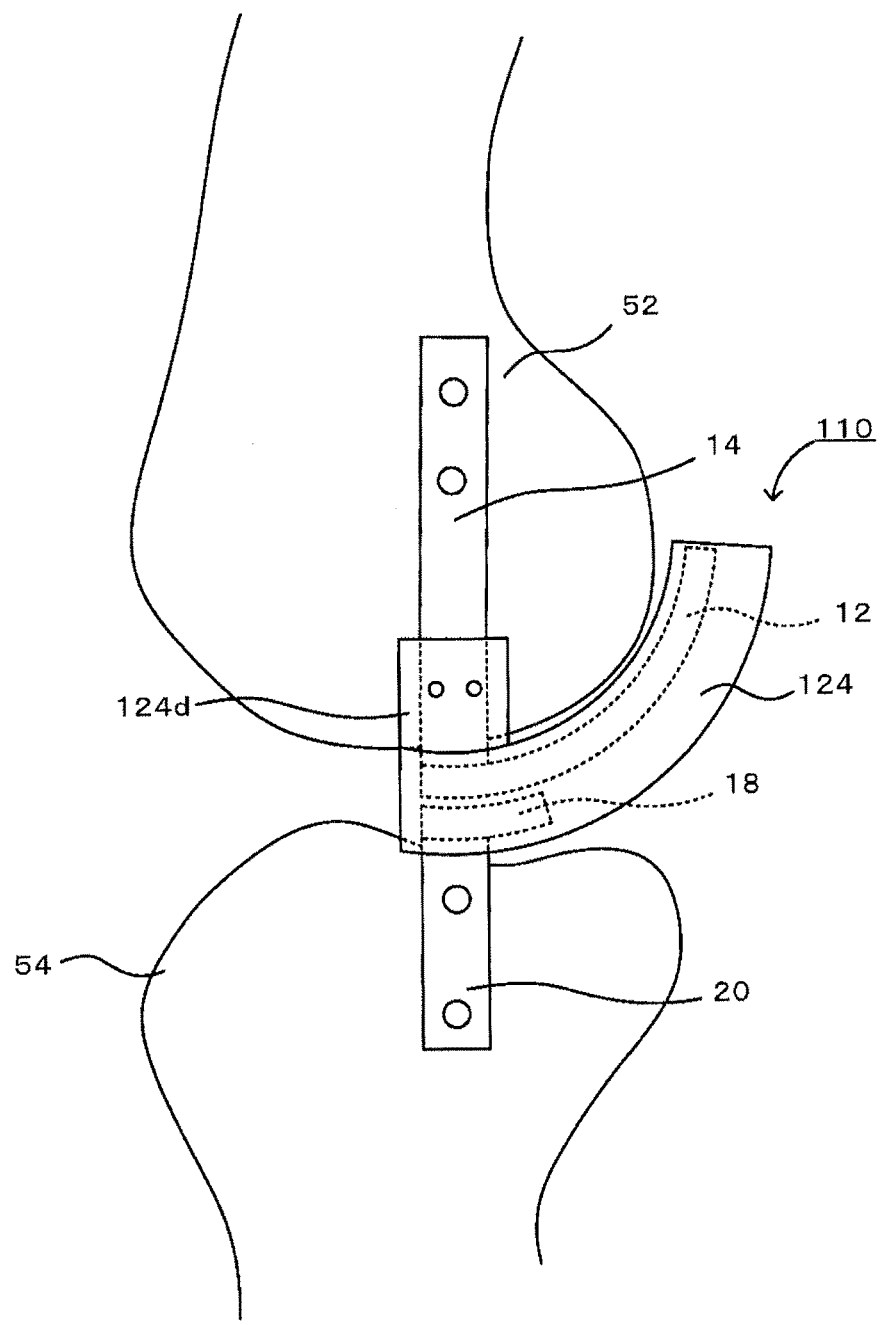
FIG. 5 is a left side view of an internal joint cavity expander 110 attached to a knee joint in the straight state.
Figure 6:
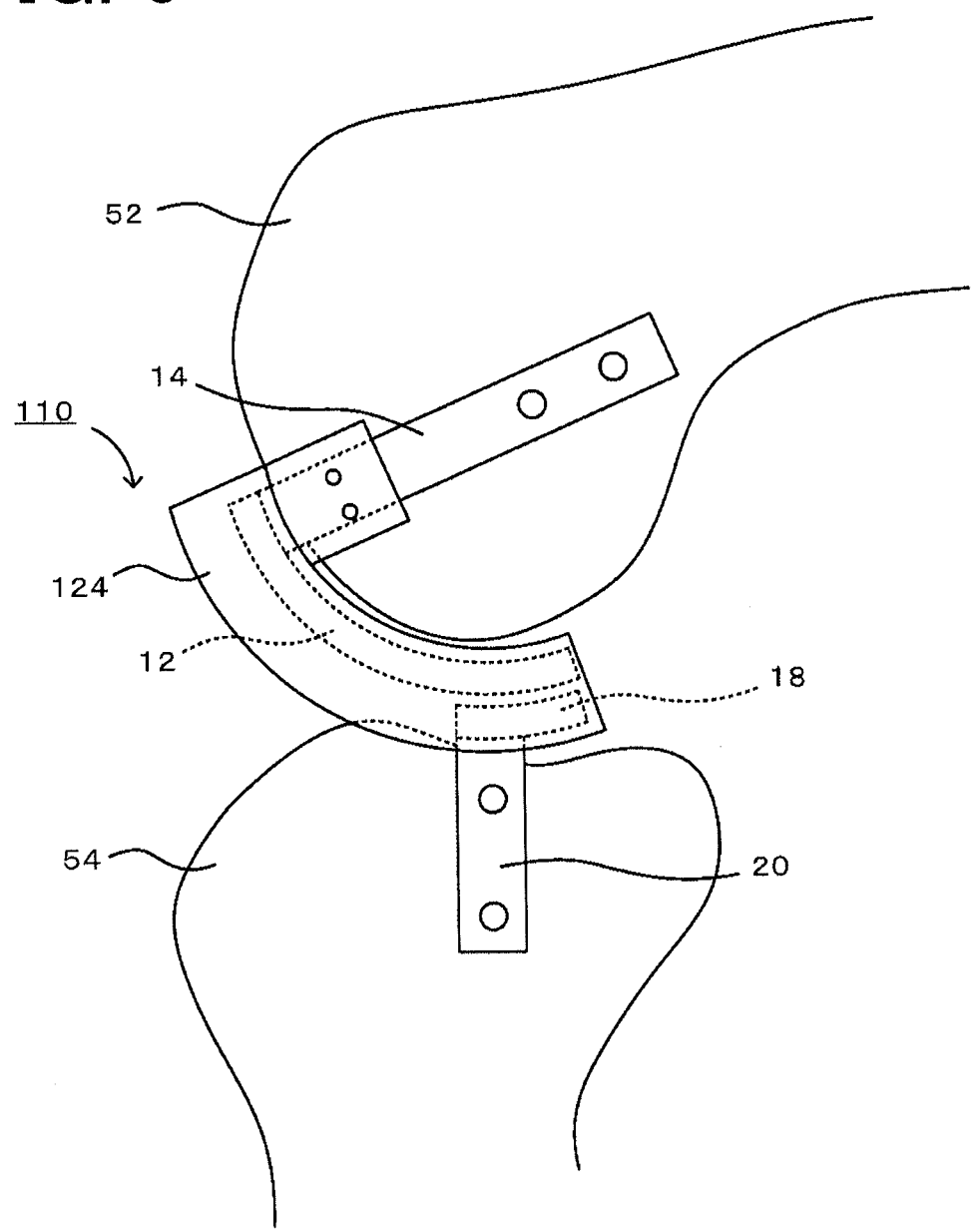
FIG. 6 a left side view of the internal joint cavity expander 110 attached to a knee joint in the bent state.

In the above-described embodiment, each magnetic shield member 24 is fixed to the corresponding tibia-side attachment piece 20. However, as in an internal joint cavity expander 110 illustrated in FIG. 5, an attachment portion 124d of each magnetic shield member 124 may be fixed to the corresponding femur-side attachment piece 14. In this case, the magnetic shield member 124 moves in accordance with the movement of the femur 52 when the knee joint is bent and stretched. Specifically, when a knee joint to which the internal joint cavity expander 110 is attached is gradually bent from the straight state, the femur 52 rotates clockwise in FIG. 5 and arrives at the bendable limit as illustrated in FIG. 6. Thus, the length of the magnetic shield member 124 suffices if the length is slightly longer than the length of the femur-side magnet 12 (the length approximately half the length of the magnetic shield member 24). Although not illustrated, each magnetic shield member 124 also includes upper and lower bent portions similar to those of the magnetic shield member 24. Both bent portions control the distance between the femur-side magnet 12 and the tibia-side magnet 18 so that the distance does not exceed a predetermined distance. In this internal joint cavity expander 110, each magnetic shield member 124 moves in accordance with the movement of the femur 52. However, since the length of each magnetic shield member 124 is small, the load imposed on the tissue around the joint as a result of the movement of the magnetic shield member 124 is not so heavy. The internal joint cavity expander 110 also has effects similar to those of the above-described embodiment.

Figure 7:
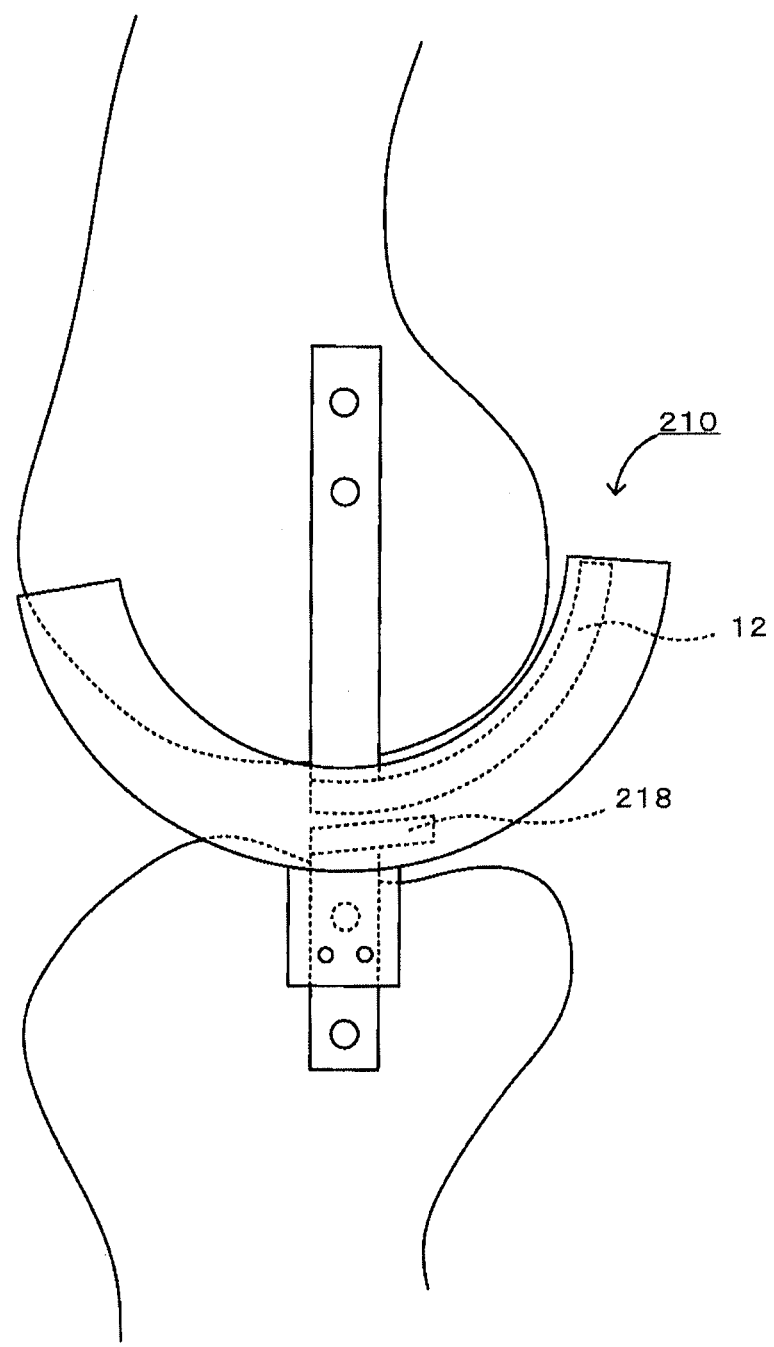
FIG. 7 is a left side view of an internal joint cavity expander 210 attached to a knee joint.

In the above-described embodiment, a magnet having a plate shape curved into an arc is used as the tibia-side magnet 18. However, as in an internal joint cavity expander 210 illustrated in FIG. 7, a magnet having a shape of a flat plate may be used as a tibia-side magnet 218. In this case, the tibia-side magnet 218 having a shape of a flat plate is designed so that the corresponding femur-side magnet 12 having an arc shape does not touch the tibia-side magnet 218 during bending and stretching movements of the knee joint. Also in this case, effects similar to those according to the embodiment are obtained.

Figure 8:
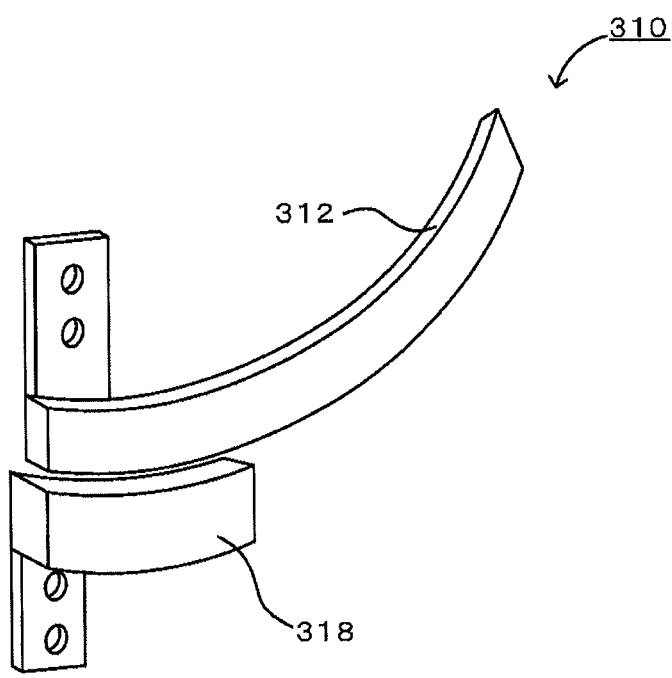
FIG. 8 is a perspective view of an internal joint cavity expander 310.

In the above-described embodiment, the upper surface and the lower surface of the femur-side magnet 12 have a larger area than the left and right side surfaces and the tibia-side magnet 18 has a shape similar to that of the femur-side magnet 12. However, as in an internal joint cavity expander 310 illustrated in FIG. 8, the upper surface and the lower surface of a femur-side magnet 312 may have a smaller area than the left and right side surfaces and a tibia-side magnet 318 may have a shape similar to that of the femur-side magnet 312. Also in this case, effects similar to those of the above-described embodiment can be obtained provided that the same pole is disposed on the convex surface of the femur-side magnet 312 and the concave surface of the tibia-side magnet 318. FIG. 8 omits illustrations of magnetic shield members.

In the above-described embodiment, the south pole is disposed on the convex surface of the femur-side magnet 12 and the concave surface of the tibia-side magnet 18. However, the north pole may be disposed on the convex surface of the femur-side magnet 12 and the concave surface of the tibia-side magnet 18.

The present application claims priority from Japanese Patent Application No. 2014-43655 filed on Mar. 6, 2014, the entire contents of which are incorporated herein by reference.

INDUSTRIAL APPLICABILITY

The present invention is usable as a medical instrument for treatment and rehabilitation of a knee joint.

REFERENCE SIGNS LIST 10 internal joint cavity expander, 12 femur-side magnet, 14 femur-side attachment piece, 16 pin, 18 tibia-side magnet, 20 tibia-side attachment piece, 22 pin, 24 magnetic shield member, 24a face member, 24b upper bent portion, 24c lower bent portion, 24d attachment portion, 26 spacer, 52 femur, 52a cartilage, 54 tibia, 54a cartilage, 110 internal joint cavity expander, 124 magnetic shield member, 124d attachment portion, 210 internal joint cavity expander, 218 tibia-side magnet, 310 internal joint cavity expander, 312 femur-side magnet, 318 tibia-side magnet.

The invention claimed is:

1. An internal joint cavity expander configured to be disposed in an incision in a knee joint to retain a space in the knee joint between a femur and a tibia, the internal joint cavity expander including at least one of each of the following components to be disposed at the left side of the knee joint, and at least another one of each of the following components to be disposed at the right side of the knee joint:
 a femur-side magnet configured to be fixed to the femur and having a shape of a plate curved into an arc so as to protrude toward the tibia when the internal joint cavity expander is disposed in the incision,
 a tibia-side magnet configured to be fixed to the tibia, being shorter in length than the femur-side magnet, and having a shape of a flat plate or a plate curved into an arc concentric with the arc of the femur-side magnet, and
 a magnetic shield member configured to be fixed to either the femur or the tibia such that the magnetic shield member is disposed so as to cover the entirety of a surface of the femur-side magnet facing a skin and the entirety of a surface of the tibia-side magnet facing the skin throughout a range in which the femur-side magnet moves relative to the tibia-side magnet, and prevents the magnetism of both magnets from leaking outside without hindering movement of the femur-side magnet relative to the tibia-side magnet,
 wherein when the internal joint cavity expander is disposed in the incision, the femur-side magnet and the tibia-side magnet on each of the left side and the right side of the knee joint are disposed so as to constantly face each other and repel each other and so that the repulsive force acts in the vertical direction while the tibia-side magnet and the femur-side magnet are moving relative to each other in response to bending and stretching movements of the knee joint.

2. The internal joint cavity expander according to claim 1, wherein on each of the left side and the right side of the knee joint, the tibia-side magnet is a magnet having a plate shape curved into an arc concentric with the arc of the femur-side magnet.

3. The internal joint cavity expander according to claim 1, wherein when the internal joint cavity expander is disposed in the incision, the magnetic shield member on each of the left side and the right side of the knee joint controls the femur-side magnet and the tibia-side magnet so that the distance between the femur-side magnet and the tibia-side magnet does not exceed a predetermined distance.

4. The internal joint cavity expander according to claim 3, wherein the magnetic shield member for each of the left side and the right side of the knee joint has a pair of bent portions which, when the internal joint cavity expander is disposed in the incision, encompass and constrain the femur-side magnet and the tibia-side magnet so that the distance between the femur-side magnet and the tibia-side magnet does not exceed the predetermined distance.

5. The internal joint cavity expander according to claim 1, further comprising, for each of the left side and the right side of the knee joint:
- a femur-side attachment piece that is integrated with the femur-side magnet, has a shape of a flat plate, and is configured to be fixed to the femur; and
- a tibia-side attachment piece that is integrated with the tibia-side magnet, has a shape of a flat plate, and is configured to be fixed to the tibia.

\* \* \* \* \*